(12) United States Patent
Scharf et al.

(10) Patent No.: US 9,156,600 B2
(45) Date of Patent: Oct. 13, 2015

(54) MODIFIED POLYIMIDES AND MOISTURE INTERACTIVE MATERIALS AND PRODUCTS INCLUDING THE SAME

(75) Inventors: Sara R. Scharf, Redondo Beach, CA (US); Randy M. Villahermosa, Los Angeles, CA (US)

(73) Assignee: The Aerospace Corporation, El Segundo, CA (US)

( * ) Notice: Subject to any disclaimer, the term of this patent is extended or adjusted under 35 U.S.C. 154(b) by 1203 days.

(21) Appl. No.: 12/266,355

(22) Filed: Nov. 6, 2008

(65) Prior Publication Data

US 2010/0108943 A1 May 6, 2010

(51) Int. Cl.
| | |
|---|---|
| C08J 3/09 | (2006.01) |
| B65D 81/26 | (2006.01) |
| B01J 20/02 | (2006.01) |
| B01J 20/26 | (2006.01) |
| B01J 20/28 | (2006.01) |
| B65D 79/02 | (2006.01) |
| G01N 31/22 | (2006.01) |
| B29K 79/00 | (2006.01) |

(52) U.S. Cl.
CPC ........... B65D 81/264 (2013.01); B01J 20/0225 (2013.01); B01J 20/0288 (2013.01); B01J 20/262 (2013.01); B01J 20/2805 (2013.01); B01J 20/28026 (2013.01); B65D 79/02 (2013.01); G01N 31/222 (2013.01); B01D 2253/202 (2013.01); B01D 2257/80 (2013.01); B01J 2220/49 (2013.01); B29K 2079/08 (2013.01)

(58) Field of Classification Search
USPC .................. 524/423, 435, 205; 523/205, 206; 252/194
See application file for complete search history.

(56) References Cited

U.S. PATENT DOCUMENTS

| | | | |
|---|---|---|---|
| 4,337,658 A | 7/1982 | Motchenbacher et al. | |
| 5,399,609 A * | 3/1995 | Moss | 524/423 |
| 6,483,324 B1 | 11/2002 | Mitter et al. | |
| 7,074,880 B2 | 7/2006 | Rhine et al. | |

OTHER PUBLICATIONS

Rancourt, Comparison of the electrical properties of polyimide films containing surface metal oxide: cobalt oxide vs. tin oxide, 1988, Thin Solis Films, 158, 189-206.*
Boggess et al., Characterization of Cobalt-Modified Polyimides, J. Poly. Sci; Part A. vol. 25, 685-702 (1987).*
Khor, E.; Taylor, L. T., "A Study of Cobalt Ion Addition to Polyimide Films," *Polymeric Materials Science and Engineering* 49, 198-202 (1983).
Rancourt, J. D.; Taylor, L. T., "Preparation and Properties of Surface Conductive Polyimide Films via In Situ Deposition of Metal Salts," *Polymeric Materials Science and Engineering* 55, 328-333 (1986).
Boggess, R. K.; Taylor, L. T., "Characterization of Cobalt-Modified Polyimides," *J. Polym. Sci. A. Polym. Chem.* 25, 685-702 (1987).
Rancourt, J. D.; Boggess, R. K.; Horning, L. S.; Taylor, L. T., "DC Electrical, Thermal, and Spectroscopic Properties of Various Condensation Polyimides Containing Surface Cobalt Oxide," *J. Electrochem. Soc.* 134, 85-92 (Jan. 1987).
Rancourt, J. D.; Taylor, L. T., "Preparation and Properties of Surface-Conductive Polyimide Films via In Situ Codeposition of Metal Salts," *Macromolecules* 20, 790-795 (Apr. 1987).
Rancourt, J. D.; Porta, G. M.; Taylor, L. T., "Comparison of the Electrical Properties of Polyimide Films Containing Surface Metal Oxide: Cobalt Oxide vs. Tin Oxide," *Thin Solid Films* 158, 189-206 (Apr. 1988).
Khor, E.; Chan, H. S. O.; Hor, T. S. Andy, "Solvent compatible cobalt ion species as additives to polyimides," *Journal of Materials Science* 24, 557-561 (Feb. 1989).
Smith, L. L.; Dillard, J. G.; Horning, L. S.; Rancourt, J. D.; Taylor, L. T.; Wightman, J. P., "Cobalt doping of a polyimide adhesive," *Int. J. Adhesion and Adhesives* 11(2), 80-86 (Apr. 1991).
Popok, V. N.; Lukashevich, M. G.;Gorbachuk, N. I.; Odzhaev, V. B.; Khaibullin, R. I.; Khaibullin, I. B., "Magnetoresistive effect and impedance spectroscopy of Co-implanted polyimide," *Physica Status Solidi (A) , Applied Research,* 203(7), 1545-1549 (Published online Apr. 7, 2006).

* cited by examiner

*Primary Examiner* — Monique Peets
(74) *Attorney, Agent, or Firm* — Henricks, Slavin & Holmes LLP

(57) ABSTRACT

Moisture interactive materials and products formed with a polyimide material that includes metal salt (e.g., cobalt salt) portions imbedded therein such that the polyimide material is capable of absorbing, permeating, and desorbing moisture and such that the polyimide material changes in color depending upon how much moisture is currently retained by the polyimide material, the polyimide material being substantially free of oxide.

29 Claims, 4 Drawing Sheets

Generic synthesis of a diamine, dianhydride, and a cobalt complex with heat to form the polyimide film. R, R' and R" would represent any chemical substructure.

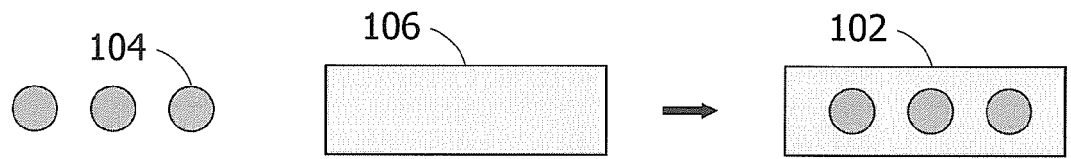
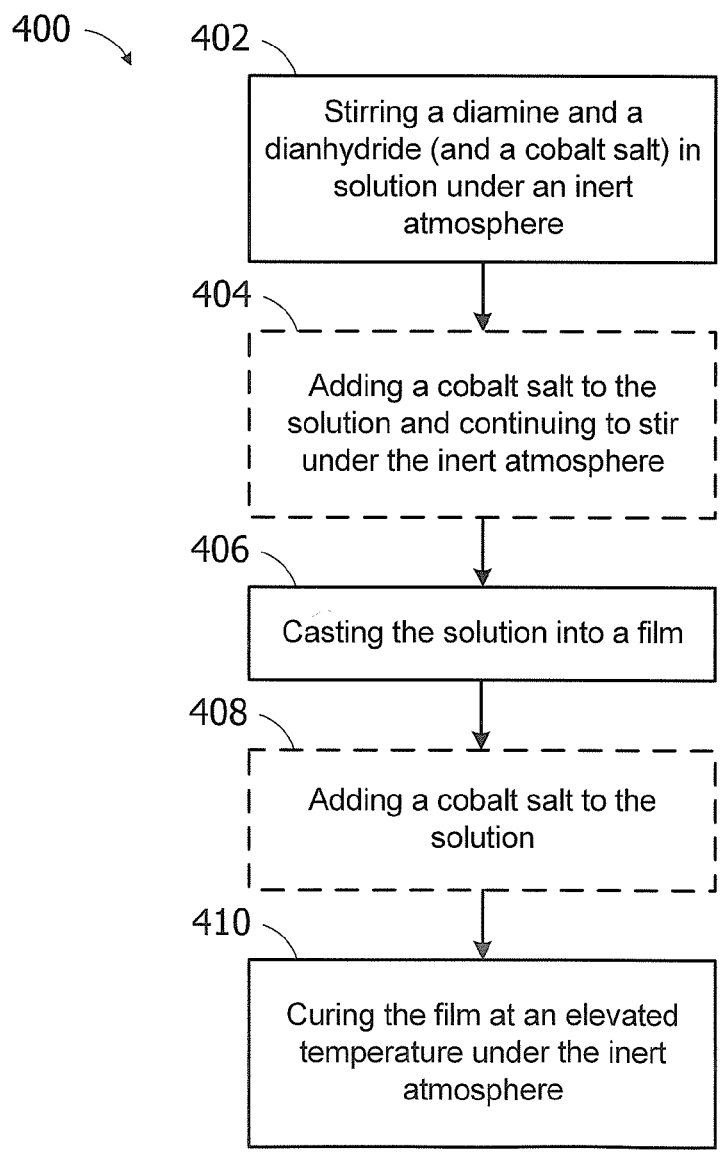

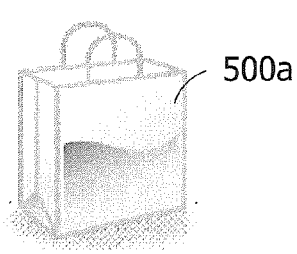
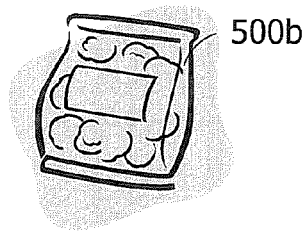
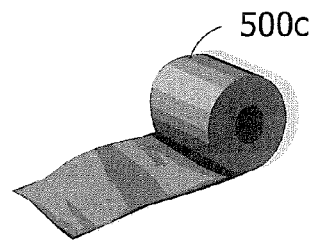
FIG. 5a        FIG. 5b        FIG. 5c
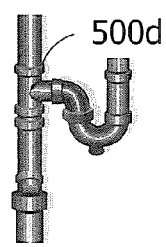
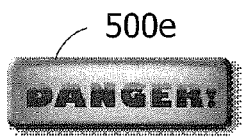
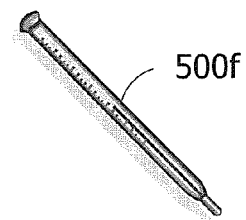
FIG. 5d        FIG. 5e        FIG. 5f
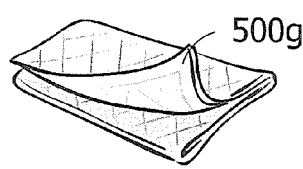
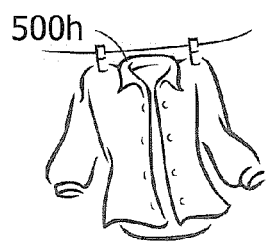
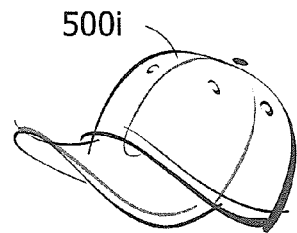
FIG. 5g        FIG. 5h        FIG. 5i

MODIFIED POLYIMIDES AND MOISTURE INTERACTIVE MATERIALS AND PRODUCTS INCLUDING THE SAME

TECHNICAL FIELD

The invention relates generally to moisture absorption and/or sensing and, in particular, to moisture interactive materials and products that include a modified polyimide material that changes color depending upon how much moisture is currently retained by the modified polyimide material.

BACKGROUND ART

A variety of moisture absorbing desiccants have been developed from materials ranging from inorganic salts to zeolites. Desiccants have also been incorporated into polymers, in an attempt to create materials that absorb moisture. There is a need, however, for materials that either absorb or control the permeation of moisture or other chemical species that are rugged, do not generate contamination, and are reusable.

Polyimides are a class of thermally and chemically stable polymers used in a variety of applications. The most well known commercially available series of polyimides are sold by DuPont™ and marketed under the trade name Kapton®. There are currently sixteen different types of Kapton® listed on the DuPont™ website. They all contain a polyimide framework but differ by their chemical or physical properties and are targeted for specific applications.

Certain polymers such as polyimides are known to absorb a small amount of water at ambient to high levels of humidity (<5%), however, they are not employed for that purpose. The use of a polymer to aid in moisture contamination has not been realized. Moisture contamination has been a general concern for many aerospace materials and systems including optical systems. Moisture as a contaminant is a common problem for space hardware, especially sensors that operate in the cryogenic temperature regime where ice formation is a possibility. Typical mitigation strategies involve the use of active thermal systems to "bake" off the water. The approach assumes a certain amount of moisture will be absorbed in porous materials, such as composite structures, thermal blankets, and other non-metallic components. While removing water on-orbit has proven effective, it is time consuming and requires intervention from a ground operator. The ability of a space grade material to sense and absorb water would be of great use, possibly eliminating or reducing the need for on-orbit bake-outs.

The synthesis of polyimides is a well-known process. By way of example, for poly(4,4'-oxydiphenylene-pyromellitimide) (Kapton® H), the synthesis begins with the condensation of a diamine with a dianhydride to form poly(amic acid). The poly(amic acid) undergoes imidization upon heating to form a polyimide. The materials are commonly cast in thin layers before heating to form thin films. Other types of polyimides can easily be prepared by making substitutions on the two building blocks (diamine and dianhydride).

Many methods for modifying polyimides have been developed. A vast amount of effort has been applied to modify well known polyimides both before and after the imidization step (i.e., heating).

It would be useful to be able to provide a moisture interactive material (i.e., moisture sensing, absorbing, permeating, reacting, detecting, capturing, and/or releasing) that has one or more of the following characteristics: excellent thermal stability, solvent resistance, good mechanical properties, radiation resistance, low thermal expansion, and wear resistance. In particular, it would be useful to be able to provide a moisture interactive material that has improved moisture absorption capacity and provides an indication of an amount of moisture presently absorbed by the material, while still retaining good mechanical properties. It would also be helpful to be able to provide an easily implemented process for synthesizing such moisture interactive materials.

SUMMARY OF THE INVENTION

Embodiments described herein relate to moisture interactive materials that have improved moisture absorption capacity and indicate an amount of moisture presently absorbed by the material, as well as methods for making such materials. Example embodiments of devices and products that include moisture interactive material are also described.

In an example embodiment, a moisture interactive material includes a polyimide material that includes metal salt (e.g., cobalt salt) portions imbedded therein such that the polyimide material is capable of absorbing, permeating, and desorbing moisture and such that the polyimide material changes in color depending upon how much moisture is currently retained by the polyimide material, the polyimide material being substantially free of oxide. In an example embodiment, the metal salt portions are evenly dispersed throughout the polyimide material.

In an example embodiment, a method for making a moisture interactive material, includes: stirring a diamine and a dianhydride in solution under an inert atmosphere; casting the solution into a film; adding a cobalt salt to the solution either before or after the solution is cast; and curing the film at an elevated temperature under the inert atmosphere. It is believed that curing under an inert atmosphere completely or substantially prevents cobalt oxide from forming in the film.

In additional example embodiments, moisture interactive apparatuses take the form of various devices and products formed from the moisture interactive materials described herein.

BRIEF DESCRIPTION OF THE DRAWINGS

FIG. 3 conceptually illustrates a polyimide material that includes cobalt salt portions imbedded therein;

FIG. 4 is a flow diagram of an example method for making a moisture interactive material;

FIG. 5a illustrates an example moisture interactive apparatus in the form of a bag (e.g., grocery bag) that includes moisture interactive material;

FIG. 5b illustrates an example moisture interactive apparatus in the form of a sealed bag (e.g., desiccant bag, or food storage bag) that includes moisture interactive material;

FIG. 5c illustrates an example moisture interactive apparatus in the form of a wrapping or packaging material that includes moisture interactive material;

FIG. 5d illustrates an example moisture interactive apparatus in the form of a tubing material that includes moisture interactive material;

FIG. 5e illustrates an example moisture interactive apparatus in the form of a labeling material that includes moisture interactive material;

FIG. 5f illustrates an example moisture interactive apparatus in the form of a moisture sensor that includes moisture interactive material;

FIG. 5g illustrates an example moisture interactive apparatus in the form of a blanket that includes moisture interactive material;

FIG. 5h illustrates an example moisture interactive apparatus in the form of an article of clothing or wearing apparel (e.g., a shirt) that includes moisture interactive material;

FIG. 5i illustrates an example moisture interactive apparatus in the form of an article of clothing or wearing apparel (e.g., a hat) that includes moisture interactive material;

DISCLOSURE OF INVENTION

Figure 1:
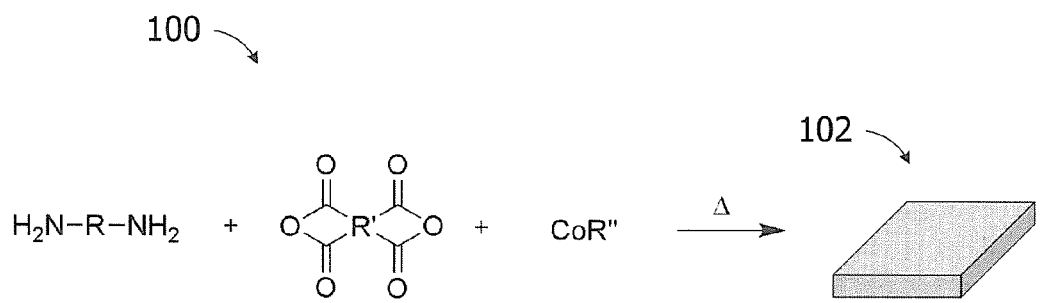
FIG. 1 illustrates an example embodiment of a generic synthesis of a diamine, dianhydride, and a cobalt complex with heat to form a polyimide film.

Referring to FIG. 1, an example synthesis 100 is shown for forming a modified polyimide film 102. In this example embodiment, a diamine, dianhydride, and a cobalt complex are combined with heat (as described below) to form a polyimide film, where R, R' and R" represent any chemical substructure.

Embodiments described herein exploit a moisture interactive material that is made in a manner that completely or substantially prevents oxide (e.g., cobalt oxide) from forming on a polyimide material that is embedded with metal salt (e.g., cobalt salt) portions. By curing the polyimide material under an inert atmosphere, the moisture interactive material is formed in a way that prevents oxidation, which is detrimental to the water interacting properties of the moisture interactive material.

Figure 2:
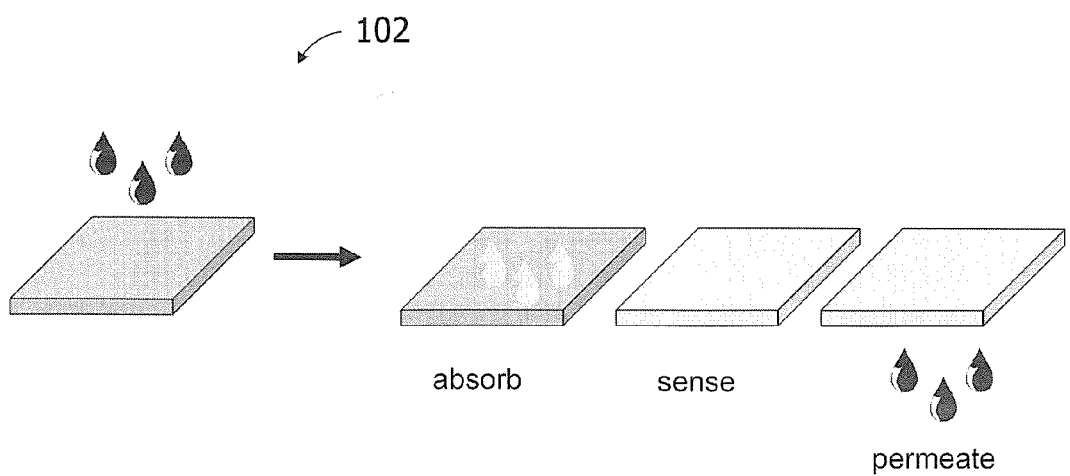
FIG. 2 conceptually illustrates functional aspects of the moisture interactive materials.

FIG. 2 conceptually illustrates functional aspects of the moisture interactive materials. The modified polyimide film 102 (e.g., cobalt-containing polyimide) is capable of absorbing, sensing, and permeating ambient moisture. The total amount of water absorption is dependent upon a number of factors including cobalt concentration; therefore, the total amount of water absorbed by a material can be tailored. The polymer undergoes a visible color change that is also proportional to the amount of water absorbed, thus also acts as a visible moisture sensor. The material can allow moisture to permeate depending on the metal concentration and humidity. The material can also reach and maintain a certain absorption level depending on the metal concentration and humidity. Subsequently when the material is retained in a dry environment, it can be mostly regenerated (dried) within a matter of a few seconds. It can be fully regenerated within a matter of a few minutes to a few hours depending on the metal concentration and material thickness.

In an example embodiment, the modified polyimide film 102 serves as a visible sensor for moisture by undergoing a color change from green to yellow or clear, depending on the diamine and dianhydride used. Water absorption by the cobalt-modified polymer is reversible through heating or by maintaining it in a low humidity environment.

FIG. 3 conceptually illustrates that a polyimide material 106 is embedded with metal salt (e.g., cobalt salt) portions 104 during synthesis to form the modified polyimide film 102. In an example embodiment, the metal salt portions are evenly dispersed throughout the polyimide material, which provides greater porosity and better physical, thermal, mechanical, and material properties.

A series of polyimides modified by adding cobalt(II) metal ions were prepared to create moisture sensing and absorbing materials. Depending on the metal concentration, the materials absorb 2-6 times or more the amount of water compared to the metal-free polymer.

An example synthesis of modified polyimide provides that two components of a polyimide (a diamine and a dianhydride) are mixed in a solution of a particular solvent. By way of example, the solvent can be N,N-dimethylacetamide but other solvents can also be used. In this example synthesis, the cobalt salt (cobalt(II) chloride hexahydrate $CoCl_2.6H_2O$) is added to the solution and it is stirred to distribute the salt. The solution is then poured out on a glass slide, or otherwise cast, and heated to very high temperatures (cured) under an inert atmosphere. The material can be easily peeled off of the glass slide to produce a film.

Referring to FIG. 4, according to example embodiments, a method 400 for making a moisture interactive material proceeds as follows. At step 402, a diamine and a dianhydride (or a diamine, a dianhydride, and a cobalt salt—alternatively, the cobalt salt can be added before or with the diamine and dianhydride into the solution) are stirred in solution under an inert atmosphere. The order of adding the cobalt salt prior to heating can be varied to either before, during, or after the diamine and dianhydride are stirred together. In example embodiments where a diamine and a dianhydride, but not a cobalt salt, are stirred in solution (at step 402), a cobalt salt is added subsequently, either at step 404, where a cobalt salt is added to the solution while continuing to stir under the inert atmosphere, or at step 408, after the solution is cast into a film at step 406. At step 408, by way of example, the cobalt salt is "dusted" across the casted polyamic acid before curing, thereby localizing the cobalt salt on one side of the film. Thus, the scope of the present invention additionally contemplates more advanced or alternative synthesis techniques where the cobalt salt is not necessarily evenly dispersed and/or is patterned, localized, etc. At step 410, the film is cured at an elevated temperature under the inert atmosphere. For example, the film is cured under nitrogen (or argon or another inert atmosphere), which is believed to preserve the cobalt(II) chloride salt that leads to the moisture sensing and absorbing capabilities, and which cobalt oxide does not possess. After the material is cured, it is not necessary to take any additional precautions to try to prevent oxidation of the cobalt. Cobalt chloride should not oxidize in air at low temperatures.

It should be understood that the scope of the present invention additionally contemplates moisture interactive materials synthesized with different polyimide components and/or metal salts.

In an example embodiment, cobalt(II) ions are introduced into the polyimide material such that the sensing and absorbing properties of the metal are retained. In this example embodiment, the synthesis begins with the formation of a poly(amic acid) using 4,4'-oxydianiline (ODA), pyromellitic dianhydride (PMDA), and N,N'-dimethylacetamide (DMAc) as the solvent. The hydrated form of cobalt(II) chloride ($CoCl_2 \cdot 6H_2O$, purple solid) as well as other types of cobalt (II) salts such as the hydrated cobalt(II) bromide ($CoBr_2 \cdot 6H_2O$, purple solid) may be used. The cobalt(II) salt was added to the viscous solution of the poly(amic acid). When the cobalt(II) salt was dissolved, the solution took on a bright blue color indicating the removal of the coordinated water molecules from the cobalt(II) ion. The stirred mixture of the poly(amic acid) and cobalt were placed directly onto Teflon® blocks or glass slides (no centrifugation needed) and cured. As the poly(amic acid) was cured through heating and the DMAc was evaporated, the material changed from a blue to a green color. The polyimides are then easily removed without the need of submerging the film in water. The final polyimide is a green color and the cobalt(II) ion is evenly dispersed. The cobalt complex does not appear to be oxidized upon curing.

Poly(amic acid) solutions of various cobalt concentrations were prepared. The solutions were drop-cast to make thin films. The films were cured in an oven following a standard curing cycle of ramping to various temperatures and maintaining that temperature for a set period of time, with a final curing temperature of 200-350° C. To make sure the metal was fully bound to the polymer, a sample of the film was submerged in an aqueous solution for a few hours. The film changed from green to clear or a yellow/orange color, the color of the metal-free polymer. Upon removal from the solution, with ample time for the polymer to dry, it changed back to the original green color and no cobalt was released into the aqueous solution. This process could be repeated multiple times, thus showing the metal is bound to the polymer, and the moisture uptake process is reversible and repeatable.

The cobalt polyimide sample had a degree of imidization of 1.0 (based on FT-IR comparison of characteristic peaks), matching the value for the metal-free polyimide thus indicating the metal-modified material was fully cured.

Differential scanning calorimetry data obtained on the polyimide films yielded an approximate $T_g$ of 300° C. indicating the material properties were not greatly perturbed by addition of the metal salt.

To quantitatively measure moisture absorption, metal-free and cobalt-modified polyimide films were cured directly onto Quartz Crystal Microbalance (QCM) mass sensors by spin-coating or drop-casting poly(amic acid) solutions and then curing them. QCM sensors were first used to determine the water absorption and desorption rate of the polyimides. A thin film of metal-free (0% Co) polyimide, which was dried prior to exposure to humidity, had a very quick initial absorption that was on the order of seconds to minutes. A thin film of 5% cobalt polyimide also had a very quick initial absorption; but the total amount of water absorbed was almost twice that of the metal-free polymer. The desorption rates for the two polymers were determined to be nearly as fast as the absorption rates.

The QCM data was also used to calculate the total amount of water absorption versus relative humidity and versus cobalt concentration. The amount of water uptake increased as the cobalt concentration increased, and the amount of water uptake increased as the humidity increased. The correlation between humidity and water uptake for metal-free polyimides is nearly linear, except for a larger increase at high humidities.

The electrical conductivity of the different polymers was measured at different humidities to determine if humidity had an effect on conductivity. Poly(amic acid) solutions with various amounts of cobalt concentrations (0 to 25%) were drop-casted on a sensor and then cured in the oven. The sensor had 50 pairs of interdigitated gold electrodes on a glass substrate with gaps of 10 µm. The conductivity increased with respect to increasing metal content, but for all polymers tested, it did not change with humidity.

As observed via FTIR and TGA data, the polymer retains most of its original physical and thermal properties after the addition of the cobalt(II) salt, which makes the material easy to substitute into existing systems that require certain characteristics of the original polymer. The differences are observed with the visible color of the polymer and with the moisture absorption capabilities, and thus the material has been enhanced and can now be used for new applications.

The cobalt-modified polyimide is initially a green color but changes to amber/yellow or clear upon exposure to moisture. The material also absorbs more moisture than the unmodified material alone. Experiments have also shown that the moisture permeation of the modified polyimide is higher then that of the unmodified polyimide.

A moisture absorbing polyimide film can also be used as an anti-static protective film. Electronic components are often sensitive to build-up and discharge of static electricity. Current technologies for preventing this problem rely on coatings that often flake off over time reducing their effectiveness and posing a contamination risk. The cobalt-modified polyimide described herein does not suffer from these drawbacks because the water-absorbing cobalt is integral to the chemical structure of the polymer.

The cobalt-modified polyimide acts as a visible sensor for the presence of moisture due to a color change from green to yellow or clear. Besides acting as a real-time indicator of moisture, it can be used as a passive (non-electrical) sensor for moisture exposure that has a memory. Similar to shock sensors attached to packages that are sensitive to damage during shipment, the cobalt-modified polyimide film can be used to indicate if an object was exposed to moisture even if it happened some time before the sensor was checked.

In additional example embodiments, moisture interactive apparatuses take the form of various devices and products formed from the moisture interactive materials described herein. The moisture interactive materials are disposed in, on, or form the devices and products. In some embodiments, a layer of moisture interactive material is secured (e.g., with an adhesive) to an underlying material, substrate of the like. In some embodiments, a layer of moisture interactive material is an outermost layer of the device or product, while in other embodiments, the moisture interactive material is internally located.

Referring to FIG. 5a, in the example embodiment, a bag 500a (e.g., grocery bag) is formed from a polyimide material described herein. Referring to FIG. 5b, in the example embodiment, a bag 500b (e.g., food storage bag, or desiccant bag) is formed from a polyimide material described herein.

The polyimide material can be useful for the transportation of foods. As reusable grocery bags have become a popular item in an attempt to reduce the amount of disposable bags, a bag made out of the moisture sensing polyimide may be useful. Even though the material absorbs and permeates a small amount of moisture, when formed into a bag, it does not allow water to "leak out". If a liquid item were to break or leak in the bag, the leak would be visible to the user by the change in the color of the bag, without the user having to remove the material. Many other reusable grocery bags made out of woven synthetic or natural fabric would leak. As the material dries, the original color would revert back and the bag could be reused.

More generally, the polyimide material can be used as a bagging material. Polyimides can withstand extreme temperatures, are flexible, can be more resistant to tearing, and produce minimal cross contamination compared to most packaging materials. The modified polyimide is also "breathable" allowing moisture to permeate through, better than other materials such as unmodified Kapton®.

Currently, a variety of fabrics and polymers are used to package desiccant materials. Paper and cloth are the most common packaging materials for desiccants. DuPont™ currently manufactures a material called Tyvek® that is more resistant to tearing and minimizes particle contamination. The modified polyimide may be superior to Tyvek® because it is also more resistant to tearing and minimizes particle contamination, but is also transparent (where Tyvek® is opaque), and has a built in moisture sensor.

Referring to FIG. 5c, in the example embodiment, a wrapping or packaging material 500c is formed from a polyimide material described herein.

Referring to FIG. 5d, in the example embodiment, a tubing material 500d is formed from a polyimide material described herein. Also, by way of example, if a tubing material used to transport water is coated with the modified polyimide, it would provide an extra layer of protection over the tubing, in addition to a visible indicator of whether there are leaks in the tubing.

Referring to FIG. 5e, in the example embodiment, a labeling material 500e is formed from a polyimide material described herein. The polyimide material can also be used for color labeling and identifying components, for example, labeling circuit boards and other moisture sensitive materials. A built-in moisture sensor in the form of a label can be positioned to identify if a particular part is currently exposed to high levels of moisture.

Referring to FIG. 5f, in the example embodiment, a moisture sensor 500f is formed from a polyimide material described herein. For example, the polyimide material can be useful as a moisture sensor for soil, gardening, and agriculture. Most moisture indicator materials are not reversible under standard conditions and they require heat and vacuum to remove the moisture. The polyimide material reversibly binds moisture and changes depending on the environment. The alternative would be expensive electronic moisture sensors.

Referring to FIG. 5g, in the example embodiment, a blanket 500g (e.g., a protective thermal blanket for a satellite) is formed from a polyimide material described herein. Removal of water from blankets or the underlying material can take a long time. While the cobalt modified polyimides have higher moisture absorption, they also quickly lose moisture upon exposure to a lower humidity environment in addition to vacuum. The modified polyimide is advantageous compared to currently available Kapton® because the time to remove water would be reduced as demonstrated by experiments where permeation was greater in the modified polyimide. This is important for satellite applications, for example, where the water must be removed before the hardware can be operated.

Figure 5J:
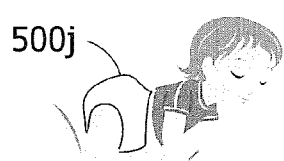
FIG. 5j illustrates an example moisture interactive apparatus in the form of an article of clothing or wearing apparel (e.g., a diaper) that includes moisture interactive material.
Figure 5K:
FIG. 5k illustrates an example moisture interactive apparatus in the form of a device for protection from the elements (e.g., an umbrella) that includes moisture interactive material.
Figure 5L:
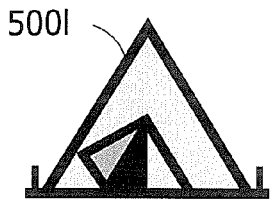
FIG. 5l illustrates an example moisture interactive apparatus in the form of a device for protection from the elements (e.g., a tent) that includes moisture interactive material.
Figure 5M:
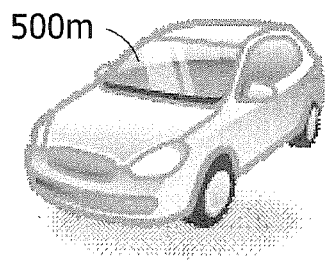
FIG. 5m illustrates an example moisture interactive apparatus in the form of a device for protection from the elements (e.g., a wind screen) that includes moisture interactive material.
Figure 5N:
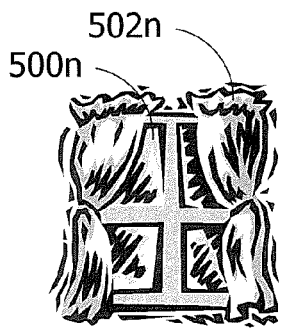
FIG. 5n illustrates an example moisture interactive apparatus in the form of a device for protection from the elements (e.g., a window and/or a curtain) that includes moisture interactive material.

In other example embodiments, articles of clothing or wearing apparel are formed from a polyimide material described herein. By way of example, FIGS. 5h, 5i and 5j show a shirt 500h, a hat 500i and a diaper 500j, respectively.

In other example embodiments, devices for protection from the elements are formed from a polyimide material described herein. By way of example, FIGS. 5k, 5l, 5m and 5n show an umbrella 500k, a tent 500l, a wind screen 500m (e.g., a film adhered to glass), and a window 500n and a curtain 502n, respectively.

Figure 5O:
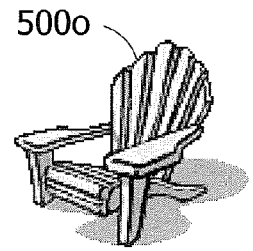
FIG. 5o illustrates an example moisture interactive apparatus in the form of an article or outdoor furniture or fixture (e.g., a deck chair) that includes moisture interactive material.

In other example embodiments, articles of outdoor furniture or fixtures are formed from a polyimide material described herein. By way of example, FIG. 5o shows a deck chair 500o.

Figure 5P:
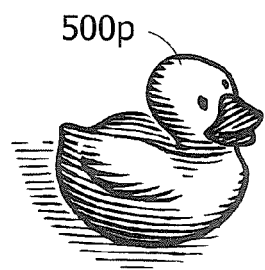
FIG. 5p illustrates an example moisture interactive apparatus in the form of a toy (e.g., a child's bath toy) that includes moisture interactive material.

In other example embodiments, toys are formed from a polyimide material described herein. By way of example, FIG. 5p shows a child's bath toy 500p.

Figure 5Q:
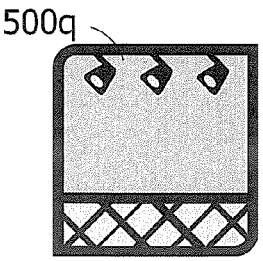
FIG. 5q illustrates an example moisture interactive apparatus in the form of a sign (e.g., a billboard) that includes moisture interactive material.

In other example embodiments, signs are formed from a polyimide material described herein. By way of example, FIG. 5q shows a billboard 500q.

Figure 5R:
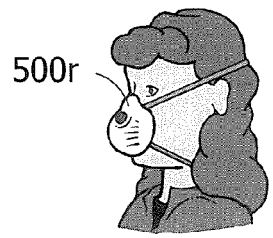
FIG. 5r illustrates an example moisture interactive apparatus in the form of a filter or membrane (e.g., a breathing mask) that includes moisture interactive material.

In other example embodiments, filters or membranes are formed from a polyimide material described herein. By way of example, FIG. 5r shows a breathing mask 500r.

Although the present invention has been described in terms of the example embodiments above, numerous modifications and/or additions to the above-described embodiments would be readily apparent to one skilled in the art. It is intended that the scope of the present invention extend to all such modifications and/or additions.

What is claimed is:

1. A moisture interactive material comprising:
   a polyimide material that includes a thermoset polyimide having metal salt portions imbedded therein and bonded to the thermoset polyimide such that the polyimide material is capable of reversibly and repeatably absorbing, permeating, and desorbing moisture and such that the polyimide material changes in color depending upon how much moisture is currently retained by the polyimide material, the polyimide material being substantially free of oxide;
   wherein the polyimide material includes poly(4,4'-oxydiphenylene-pyromellitimide).

2. The moisture interactive material of claim 1, wherein the metal salt portions include a cobalt salt.

3. The moisture interactive material of claim 1, wherein the metal salt portions include a cobalt(II) salt.

4. The moisture interactive material of claim 1, wherein the metal salt portions are evenly dispersed throughout the polyimide material.

5. The moisture interactive material of claim 1, wherein the bag is a grocery bag.

6. The moisture interactive material of claim 1, wherein the bag is a food storage bag.

7. The moisture interactive material of claim 1, wherein the bag is a desiccant bag.

8. The moisture interactive material of claim 1, the polyimide material being formed as a wrapping or packaging material.

9. The moisture interactive material of claim 1, the polyimide material being formed as a tubing material.

10. The moisture interactive material of claim 1, the polyimide material being formed as a labeling material.

11. The moisture interactive material of claim 1, the polyimide material being formed as a moisture sensor.

12. The moisture interactive material of claim 1, the polyimide material being formed as a blanket.

13. The moisture interactive material of claim 12, wherein the blanket is a bake-out blanket for a satellite.

14. The moisture interactive material of claim 1, the polyimide material being formed as an article of clothing or wearing apparel.

15. The moisture interactive material of claim 14, wherein the article of clothing or wearing apparel is a diaper.

16. The moisture interactive material of claim 1, the polyimide material being formed as a device for protection from the elements.

17. The moisture interactive material of claim 16, wherein the device for protection from the elements is an umbrella.

18. The moisture interactive material of claim 16, wherein the device for protection from the elements is a tent.

19. The moisture interactive material of claim 16, wherein the device for protection from the elements is a window or wind screen.

20. The moisture interactive material of claim 16, wherein the device for protection from the elements is a curtain.

21. The moisture interactive material of claim 1, the polyimide material being formed as an article of outdoor furniture or fixture.

22. The moisture interactive material of claim 1, the polyimide material being formed as a toy.

23. The moisture interactive material of claim 22, wherein the toy is a child's bath toy.

24. The moisture interactive material of claim 1, the polyimide material being formed as a sign.

25. The moisture interactive material of claim 1, the polyimide material being formed as a filter or membrane.

26. A moisture interactive material comprising:
a polyimide material that includes a thermoset polyimide having metal salt portions imbedded therein and bonded to the thermoset polyimide such that the polyimide material is capable of reversibly and repeatably absorbing, permeating, and desorbing moisture and such that the polyimide material changes in color depending upon how much moisture is currently retained by the polyimide material, the polyimide material being substantially free of metal oxide;
wherein the polyimide material includes poly(4,4'-oxydiphenylene-pyromellitimide).

27. The moisture interactive material of claim 26, wherein the metal salt portions include a cobalt salt.

28. The moisture interactive material of claim 26, wherein the metal salt portions include a cobalt(II) salt.

29. The moisture interactive material of claim 26, wherein the metal salt portions are evenly dispersed throughout the polyimide material.

* * * * *